United States Patent
Rakshit

(10) Patent No.: US 11,464,464 B2
(45) Date of Patent: Oct. 11, 2022

(54) INTERNAL AND EXTERNAL PROXIMATE SCANNING

(71) Applicant: International Business Machines Corporation, Armonk, NY (US)

(72) Inventor: Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/937,848

(22) Filed: Jul. 24, 2020

(65) Prior Publication Data

US 2022/0022822 A1 Jan. 27, 2022

(51) Int. Cl.
*A61B 6/03* (2006.01)
*A61B 6/00* (2006.01)
*A61B 8/12* (2006.01)
*A61B 6/02* (2006.01)

(52) U.S. Cl.
CPC ............. *A61B 6/032* (2013.01); *A61B 6/027* (2013.01); *A61B 6/488* (2013.01); *A61B 6/542* (2013.01); *A61B 8/12* (2013.01)

(58) Field of Classification Search
CPC ......... A61B 6/027; A61B 6/032; A61B 6/488; A61B 6/542; A61B 8/12
See application file for complete search history.

(56) References Cited

U.S. PATENT DOCUMENTS

| | | | |
|---|---|---|---|
| 2003/0073895 A1* | 4/2003 | Nields | A61B 8/469 600/407 |
| 2005/0036059 A1 | 2/2005 | Goldwasser | |
| 2007/0036750 A1* | 2/2007 | Chou | A61P 9/00 424/85.1 |
| 2010/0091937 A1* | 4/2010 | Raupach | A61B 6/4035 378/150 |
| 2010/0239144 A1* | 9/2010 | Fichtinger | A61B 8/5238 382/131 |
| 2011/0004059 A1* | 1/2011 | Arneson | A61B 1/00045 600/109 |
| 2012/0051498 A1* | 3/2012 | Koishi | A61B 6/5205 378/10 |

(Continued)

FOREIGN PATENT DOCUMENTS

CN 106388843 A 2/2017
CN 109381212 A 2/2019
(Continued)

OTHER PUBLICATIONS

Camps, S.M. et al., "The Use of Ultrasound Imaging in the External Beam Radiotherapy Workflow of Prostate Cancer Patients", BioMed Research International, vol. 2018, 7569590:1-16 (Year: 2018).*

(Continued)

*Primary Examiner* — Blake C Riddick
(74) *Attorney, Agent, or Firm* — Jared C. Chaney

(57) ABSTRACT

Aspects of the present disclosure relate to internal and external scanning. In some embodiments, the method includes receiving a first set of data from an ingestible scanning device inside a body, identifying a first point of interest within the body based on the data, determining a location of a first point of interest within the body, and scanning the point of interest with an external scanning device.

20 Claims, 6 Drawing Sheets

(56) References Cited

U.S. PATENT DOCUMENTS

| | | | | |
|---|---|---|---|---|
| 2012/0140874 | A1* | 6/2012 | Li | A61B 6/032 378/11 |
| 2015/0139395 | A1* | 5/2015 | Yl | A61B 6/4035 378/62 |
| 2015/0294454 | A1* | 10/2015 | Nempont | A61B 6/5247 382/128 |
| 2016/0100970 | A1* | 4/2016 | Brister | A61F 5/003 606/192 |
| 2016/0206266 | A1* | 7/2016 | Lee | G06T 5/008 |
| 2016/0278662 | A1* | 9/2016 | Brister | A61B 1/041 |
| 2017/0086775 | A1* | 3/2017 | Madhav | A61B 6/4035 |
| 2018/0153385 | A1 | 6/2018 | Arneson | |
| 2019/0015070 | A1 | 1/2019 | Memon et al. | |
| 2019/0021629 | A1* | 1/2019 | Calzi | A61B 5/073 |
| 2019/0206051 | A1 | 7/2019 | Cao | |
| 2019/0261920 | A1* | 8/2019 | Euliano | A61B 5/065 |
| 2020/0170598 | A1* | 6/2020 | Shea | A61B 6/4078 |

FOREIGN PATENT DOCUMENTS

| | | |
|---|---|---|
| CN | 110598696 A | 12/2019 |
| WO | 2019014228 A1 | 1/2019 |

OTHER PUBLICATIONS

Kalantar-Zadeh et al., "Ingestible Sensors," ACS Sensors, © 2017 American Chemical Society, 16 pages https://pubs.acs.org/doi/pdf/10.1021/acssensors.7b00045.

Frost & Sullivan, "Conventional Medical Imaging Modalities Facing Disruption," Aug. 13, 2018, 14 pages https://ww2.frost.com/frost-perspectives/conventional-medical-imaging-modalities-facing-disruption/.

"General Nuclear Medicine," RadiologyInfo.org., Copyright © 2019 Radiological Society of North America, Inc. (RSNA), 10 pages, https://www.radiologyinfo.org/en/info.cfm?pg=gennuclear.

"What's the Difference Between Ultrasounds and X-rays?" Diagnostic Medical Sonography, Ultrasound Schools Info, 2020 © UltrasoundSchoolsInfo.com., 13 pages https://www.ultrasoundschoolsinfo.com/whats-the-difference-between-ultrasounds-and-x-rays/.

Lafer, "Ultrasound or Radiographs (x-rays)—What's the Difference?" Feline Docs, Feb. 21, 2013, 4 pages http://felinedocs.com/dr-diana-lafer/ultrasound-or-radiographs-x-rays-%E2%80%93-what%E2%80%99s-the-difference/.

"Capsule endoscopy," Mayo Clinic, © 1998-2020 Mayo Foundation for Medical Education and Research (MFMER), Printed Feb. 3, 2020, 6 pages, https://www.mayoclinic.org/tests-procedures/capsule-endoscopy/about/pac-20393366.

"CT scan is no more accurate than ultrasound to detect kidney stones, study finds," Science Daily, Science News, Sep. 17, 2014, 4 pages, https://www.sciencedaily.com/releases/2014/09/140917173235.htm.

Mehta, "Ask Dr. M: What's the difference between an X-ray, CT scan, ultrasound, and MRI?" Medium, Jan. 29, 2019, 8 pages, https://medium.com/@dothealth/ask-dr-m-whats-the-difference-between-an-x-ray-ct-scan-ultrasound-and-mri-b7df58549c3c.

Cox et al., "Ultrasound capsule endoscopy: sounding out the future," ATM Annals of Translational Medicine, vol. 5, No. 9, May 2017, 15 pages, http://atm.amegroups.com/article/view/14711/html.

Mell et al., "The NIST Definition of Cloud Computing," Recommendations of the National Institute of Standards and Technology, U.S. Department of Commerce, Special Publication 800-145, Sep. 2011, 7 pages.

Rakshit, "Internal and External Proximate Scanning," International Application No. PCT/CN2021/099130, filed Jun. 9, 2021, IBM Docket No. P201906371PCT01.

* cited by examiner

INTERNAL AND EXTERNAL PROXIMATE SCANNING

BACKGROUND

Aspects of the present disclosure relate to internal and external proximate scanning; more particular aspects relate to medical device scanning.

Medical scanning is the technique and process of collecting data of the interior of a body for clinical analysis and medical intervention, as well as visual representation of the function of some organs or tissues (physiology). Medical scanning may reveal internal structures hidden by the skin and bones, as well as to diagnose and treat disease. Medical scanning also establishes a database of normal anatomy and physiology to make it possible to identify abnormalities or anomalies. In the case of medical ultrasound, a probe emits ultrasonic pressure waves and echoes that go inside the tissue to show the internal structure. In the case of projectional radiography, the probe uses X-ray radiation, which is absorbed at different rates by different tissue types such as bone, muscle, and fat.

Medical scanning includes radiology procedures, which use the imaging technologies of X-ray radiography, magnetic resonance imaging, ultrasound, endoscopy, elastography, tactile imaging, thermography, medical photography, and nuclear medicine functional imaging techniques as positron emission tomography (PET) and single-photon emission computed tomography (SPECT), among others.

Medical scanning also includes measurement and recording techniques that are not primarily designed to produce images, such as electroencephalography (EEG), magnetoencephalography (MEG), electrocardiography (ECG), and others.

SUMMARY

The present disclosure provides a method, computer program product, and system of internal and external proximate scanning. In some embodiments, the method includes receiving a first set of data from an ingestible scanning device inside a body, identifying a first point of interest within the body based on the first set if data, determining a location of the first point of interest within the body, and scanning the point of interest with an external scanning device.

In some embodiments, the computer program product includes a computer readable storage medium having program instructions embodied therewith, the program instructions executable by a computer to cause the computer to receive a first set of data from an ingestible scanning device inside a body of a patient; identify a point of interest within the body based on the first set of data; determine a location of the point of interest within the body; and scan the point of interest with an external scanning device.

In some embodiments, the system includes a processor; and a memory in communication with the processor, the memory containing program instructions that, when executed by the processor, are configured to cause the processor to perform a method, the method comprising receiving a first set of data from an ingestible scanning device inside a body of a patient; identifying a point of interest within the body based on the first set of data; determining a location of the point of interest within the body; and scanning the point of interest with an external scanning device.

DETAILED DESCRIPTION

Figure 1:
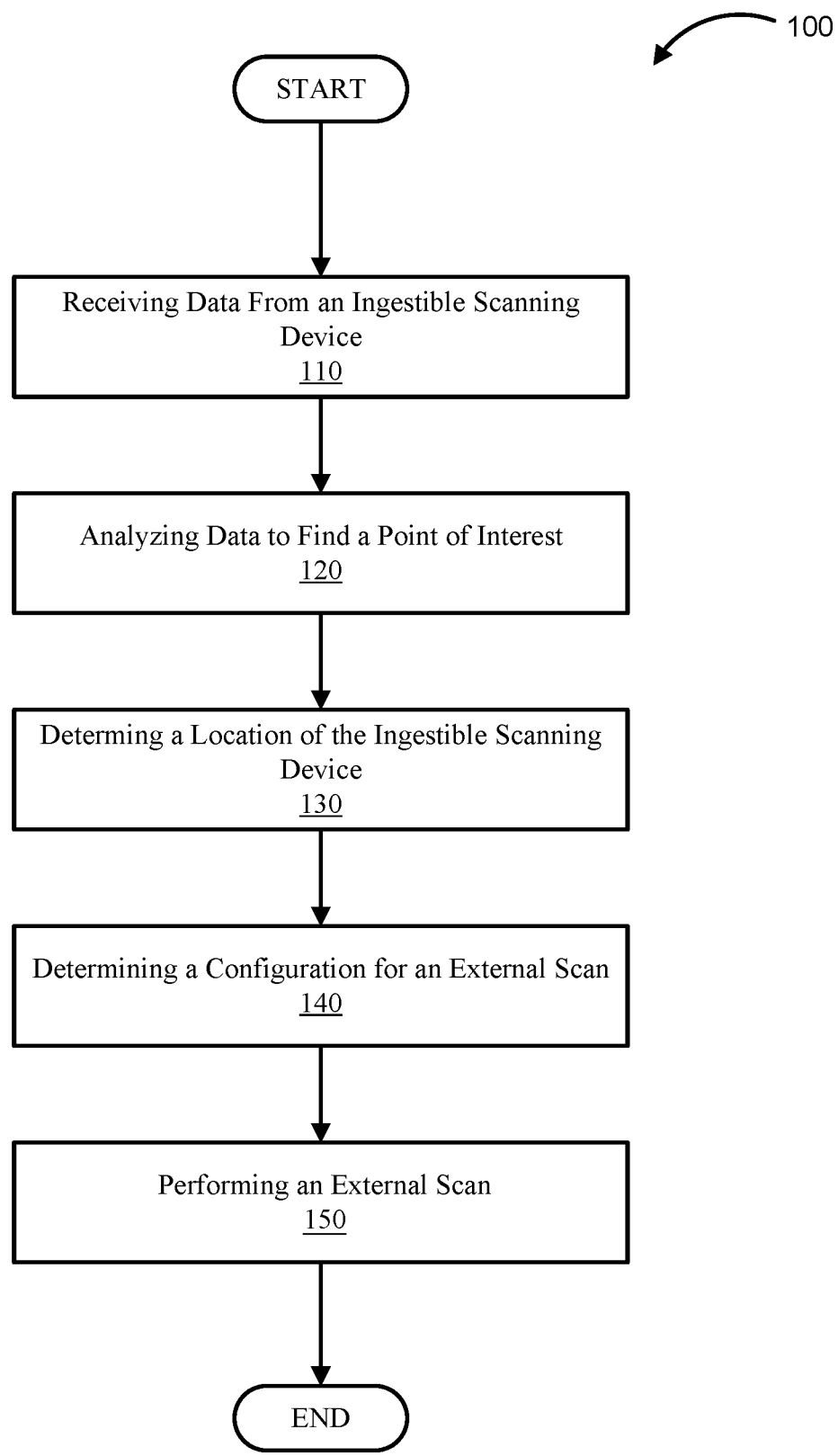
FIG. 1 illustrates a flowchart of an example method of internal and external proximate scanning according to various embodiments of the present disclosure.

Medical scans such as x-rays, ultrasounds, CT scans, MRI scans, etc. give valuable information, but may individually not give the whole picture. For example, x-rays in medical diagnosis are normally used to obtain a visual image of the subject radiographed. The image results from the differential attenuation of the radiation, which depends in part on the thickness, density, and orientation of the organ irradiated and in part on the proportion and nature of the different chemical elements present. The nature of biological material is such that the contrast differentiation between organs or parts of an organ is frequently poor and, despite methods to increase the contrast, this remains one of the principal limitations. Additional limitations are imposed when living subjects are examined since movement of the subject may seldom be eliminated and movement may distort images. Additionally, because imaging radiation may be harmful to living subjects, it is preferable to keep the radiation dose as low as reasonably practical. Further constraints are imposed by the high cost of some equipment and the shortage of qualified manpower to operate the equipment and interpret the findings. It is important to provide radiologists with only the most relevant and informational images possible. Furthermore, the number and type of examinations carried out may have to be limited in some very sick patients because they reach their limits of endurance. Practically every procedure therefore has specific advantages and limitations. However, with internal and external proximate scanning some of the limitations may be mitigated and a more complete understanding of a scanned target may be achieved.

The medical community is continuing to make advancements in medical scanning technology. However, sometimes lack of information may cause overuse, impreciseness, and incorrect diagnosis. For example, without knowing the exact location of interest (e.g., a growth), a general area x-ray or CT scan may be used instead of a localized precise scan. This may lead to excess exposure to harmful elements such as radiation, extra expense, and wasted time for doctors in viewing images and results.

In some embodiments, a system for using an internal scanning technique (e.g., an ingestible scanning device) in conjunction with an external scanning technique is proposed. By combining an internal scanning technique (e.g., an ingestible ultrasonic pill) and an external scan (e.g., an x-ray), a more focused and efficient process may be achieved. By combining the scans, the disadvantages of one or both of the individual scans may be mitigated. For example, where normally a broad range x-ray may be used, an ingestible scanning device may be used to tell the medical technician exactly where the x-ray needs to be taken. With that information, the medical technician may use a narrow-range x-ray on that location thereby limiting the area of exposure. Likewise, by using two different scanning methods and correlating the results, a more complete picture of the area of interest may be determined. In some embodiments, a first internal scanning device may provide information so that a second external scan may be selected or configured. For example, some points of interest may be more accurately analyzed by an MRI and some may be more accurately analyzed by an x-ray.

FIG. 1 shows an example method 100 for internal and external proximate scanning. The example method 100 depicts a model for performing proximate scans of a live body.

In block 110, scanning data from an ingestible scanning device is received. In some embodiments, the ingestible scanning device may be a wireless device that may take scans (e.g., ultrasonic scans/images, video, pictures, temperature, etc.) of the internal body, send signals, receive signals, and/or make recordings. In some embodiments, the ingestible scanning device takes scans continually. In some embodiments, the ingestible scanning device takes scans after specific triggers. For example, the ingestible scanning device may be configured to take scans only after passing through the stomach, at set time intervals, or after receiving an outside signal.

In some embodiments, the ingestible scanning device is used to describe a piece of scanning equipment that may be swallowed. In some embodiments, the ingestible scanning device may be an ultrasonic capsule. Ultrasound capsule endoscopy (USCE) overcomes surface-only imaging limitations and provides transmural scans of the GI tract. The integration of high frequency microultrasound ($\mu$US) into capsule endoscopy allows high resolution transmural images and provides a means of both qualitative and quantitative assessment of the bowel wall.

In some embodiments, the ingestible scanning device may be any other capsule with scanning capabilities. For example, capsule endoscopy is a procedure that uses a tiny wireless camera to take pictures of a digestive tract. A capsule endoscopy camera sits inside a vitamin-size capsule that is swallowed. As the capsule travels through the digestive tract, the camera takes thousands of pictures that are transmitted to a recorder.

In block 120, the data from the ingestible scanning device is analyzed to find a point of interest. In some embodiments, the point of interest may be a particular target area that is previously determined. For example, the point of interest may be an ulcer that a patient is complaining of, a tumor previously found, or a growth found by the ingestible scanning device. In some embodiments, the point of interest may be any area that exhibits anomalous characteristics. In some embodiments, the location and characteristics (e.g., size, shape, density, etc.) of a point of interest may be used to determine what further scans/testing should be used and how the scans/testing should be configured. In some embodiments, the data may be analyzed for information indicative of a point of interest (e.g., an anomaly). For example, the system may have reading thresholds that may be indicative of one or more target features. Some instances of reading thresholds may be shape, density, signal transmission, opaqueness, and/or signal reflection. For example, kidney stones and tumors refract ultrasonic images more strongly than soft tissue. For example, certain shapes of growths in the intestine may indicate cancerous growths. In some embodiments, the data may be analyzed by an artificial neural network.

Artificial neural networks (ANNs) may be computing systems modeled after the biological neural networks found in animal brains. Such systems learn (i.e., progressively improve performance) to do tasks by considering examples, generally without task-specific programming. For example, in image recognition, ANNs might learn to identify images that contain tumors by analyzing example images that have been manually labeled as "tumor" or "no tumor" and using the analytic results to identify tumors in other images.

In some embodiments of the present disclosure, neural networks may be used to identify points of interest in data scans. Neural networks may be trained to recognize patterns in input data by a repeated process of propagating training data through the network, identifying output errors, and altering the network to address the output error. Training data may be propagated through the neural network, which recognizes patterns in the training data. Those patterns may be compared to patterns identified in the training data by human annotators in order to assess the accuracy of the neural network. In some embodiments, mismatches between the patterns identified by a neural network and the patterns identified by human annotators may trigger a review of the neural network architecture to determine the particular neurons in the network that contribute to the mismatch. Those particular neurons may then be updated (e.g., by updating the weights applied to the function at those neurons) in an attempt to reduce the particular neurons' contributions to the mismatch. In some embodiments, random changes are made to update the neurons. This process may be repeated until the number of neurons contributing to the pattern mismatch is slowly reduced, and eventually, the output of the neural network changes as a result. If that new output matches the expected output based on the review by the human annotators, the neural network is said to have been trained on that data.

In some embodiments, once a neural network has been sufficiently trained on training data sets for a particular subject matter, it may be used to detect patterns in analogous sets of live data (i.e., non-training data that has not been previously reviewed by human annotators, but that are related to the same subject matter as the training data). The neural network's pattern recognition capabilities may then be used for a variety of applications. For example, a neural network that is trained on a particular subject matter may be configured to review live data for that subject matter and predict the probability that a potential future event associated with that subject matter may occur.

In some embodiments, a multilayer perceptron (MLP) is a class of feedforward artificial neural networks. An MLP consists of, at least, three layers of nodes: an input layer, a hidden layer, and an output layer. Except for the input nodes, each node is a neuron that uses a nonlinear activation function. MLP utilizes a supervised learning technique called backpropagation for training. Its multiple layers and non-linear activation distinguish MLP from a linear perceptron. It may distinguish data that is not linearly separable. Also, MLP may be applied to perform regression operations.

Accurate identification of points of interest in data scans (such as an ultrasound image) relies on processing live data sets that contain large amounts of data. For example, live data sets may include various sources of biological data (such ultrasound images, pictures, x-ray images, temperature, acidity, etc.). Further, achieving accurate predictions for some subject matters is difficult due to the amount of data that may be relevant to a prediction. For example, an ultrasound pill may take thousands of scans as it passes through the digestive system. In some embodiments, for example, a neural network in accordance with the present disclosure may be configured to generate a prediction of the probability of a point of interest (i.e., the event for which a probability is sought in a target prediction) related to a particular set of conditions for a line asset. For example, in some embodiments, a predictive neural network may be utilized to predict the numerical probability that a particular section of intestine contains an anomaly (e.g., the predictive neural network would identify an anomaly as a point of interest) that warrants an external scan by an external scanning device.

In block 130, the location and/or orientation of the ingestible scanning device may be determined. In some embodiments, the scanning data may be used to determine the location. For example, tissue scans performed by an ultrasonic ingestible scanning device may identify its surrounding environment as the stomach, small intestine, or large intestine. This identification can then be used to determine the location of the scanning device. For example, in some embodiments, the ingestible device may use a tissue scan to determine its location. In some embodiments, the ingestible scanning device may send images to an external computer system and the external computer system may determine where the ingestible device is based on the images received. In some embodiments, the location of the point of interest may also be determined.

A variety of methods may be performed to determine the pill's location. In some embodiments, the determining of the location may be performed by a technique selected from the group consisting of x-ray detection, ultrasound detection, echolocation, doppler location, triangulation, or some combination thereof.

In some embodiments, an x-ray may be used to determine the location. This may be a specialized x-ray specifically designed to locate the pill. For example, if the pill is made, at least partially, from metal, it may stand out distinctly even on a low power x-ray.

A pulse-doppler radar is a radar system that determines the range to a target using pulse-timing techniques, and uses the doppler effect of the returned signal to determine the target object's velocity. It combines the features of pulse radars and continuous-wave radars, which were formerly separate due to the complexity of the electronics.

Ultrasound scanners consist of a computer console, video display screen and an attached transducer. The transducer is a small hand-held device that resembles a microphone. Some exams may use different transducers (with different capabilities) during a single exam. The transducer sends out inaudible, high-frequency sound waves into the body and then listens for the returning echoes. The principles are similar to sonar used by boats and submarines.

Triangulation is a process by which the location of a radio transmitter may be determined by measuring either the radial distance, or the direction, of the received signal from two or three different points. Triangulation is sometimes used in cellular communications to pinpoint the geographic position of a user.

In block 140, a configuration for an external scan may be determined based on the information received from the ingestible scanning device and/or the location of the ingestible scanning device. In some embodiments, the external scanning device may be positioned to produce better images. For example, if an ingestible scanning device identifies low blood flow in a certain area of the intestine, it may be determined that a specific orientation for an x-ray exposure may give the most relevant data. Likewise, the configuration may include one or more settings for an external scan, such as orientation, intensity, area of exposure, exposure duration, etc. For example, images received from an ultrasound pill may identify a certain area of the intestines that needs an external scan. Likewise, the location and orientation of the pill may help determine the settings for the external scan. The exact location where the ingestible scanning device took an image and the orientation of the ingestible scanning device may be used to direct an external device to an exact location to scan in the body. For example, the human intestinal tract is about 25 ft long, identifying the exact location and orientation of the ingestible scanning device when it detected a point of interest (e.g., an anomaly) may allow a much narrower external scan to be performed.

In some embodiments, the configuration of the external scan may include the type of scan to be performed. In some embodiments, the location and characteristics (e.g., low blood flow, calcification, etc.) of the point of interest may be used to determine what kind of external scan may be used. For example, for a point of interest with high calcification, an x-ray may be a better choice than an MRI.

At block 150, an external scan may be performed. In some embodiments, the scan may be synchronous; the ingestible scanning device may scan a point of interest and the external scanning device may scan the point of interest at the same approximate time. Synchronous scanning may occur when the point of interest has been previously identified. For example, when an a point of interest is known, the external scanning device may be on standby until the ingestible scanning device is in place and then both may take an image at approximately the same time. In some embodiments, the external device may be on standby waiting for the ingestible scanning device to detect a point of interest. For example, as the ingestible scanning device is traveling through the digestive track, an external device may be following its progression through the body. If the ingestible scanning device detects a point of interest, the external scanning device may scan the point of interest area almost immediately. In some embodiments, the ingestible scanning device detects a point of interest and an external scan may be subsequently performed. For example, if an ingestible scanning device detects a point of interest at a certain location, the location may be identified and a subsequent external scan of the area may be performed based on the location and the data received from the ingestible scanning device.

In some embodiments, the data from the ingestible scanning device and the external scan may be compared. Scans may be compared and correlated to obtain more information about the point of interest. For example, a shape and blood flow may be obtained from the ingestible scanning device, and a density may be obtained from the external scanning device.

Figure 2:
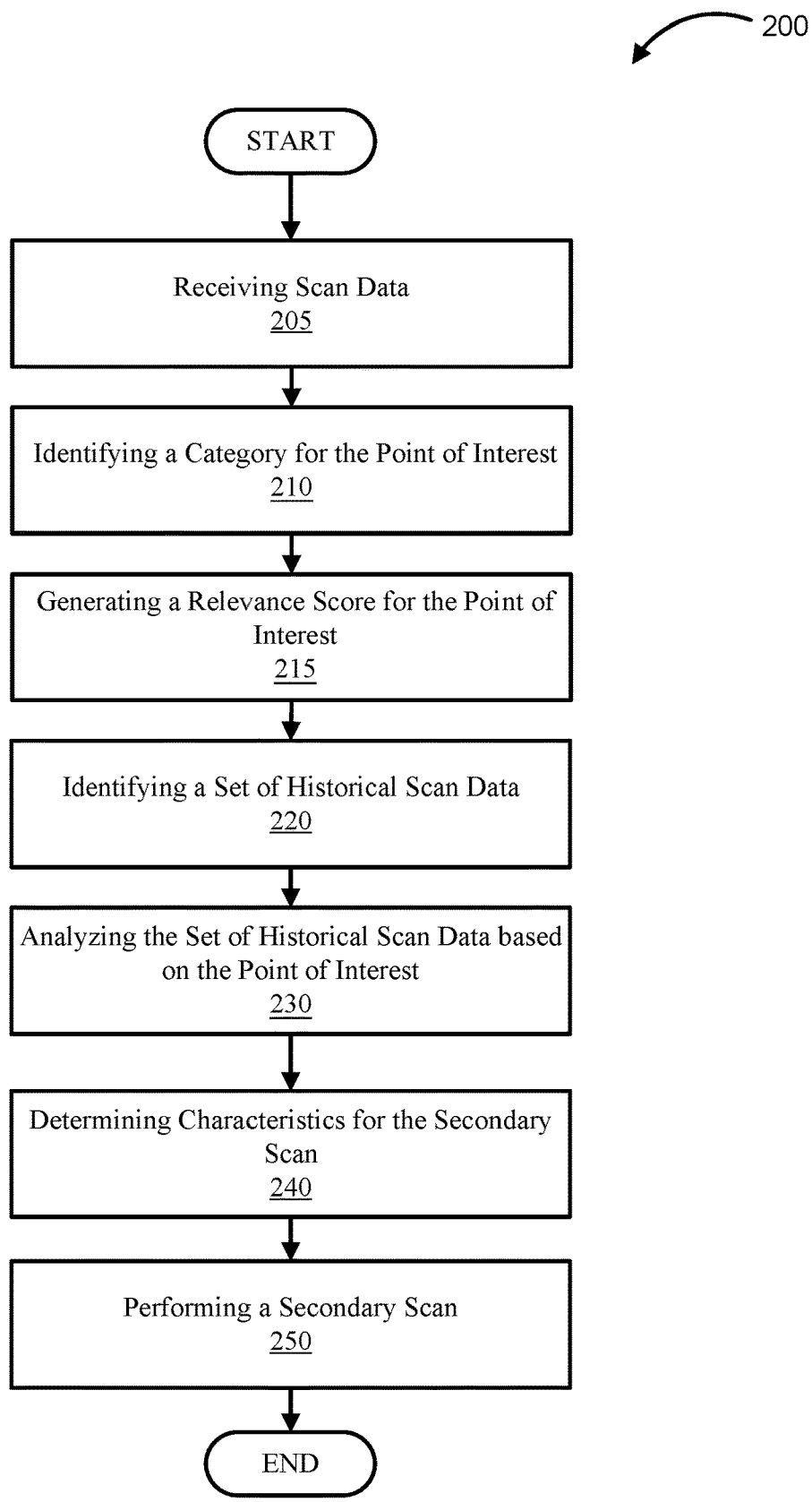
FIG. 2 illustrates a flowchart of an example method for configuring an external scan based on an internal scan and historical data according to various embodiments of the present disclosure.

FIG. 2 illustrates a flowchart of an example method 200 for configuring an external scan based on an internal scan and historical data, in accordance with embodiments of the present disclosure.

In some embodiments, historical data includes previous scans and their outcomes. In some embodiments, historical data may indicate what identified features that may be important in a point of interest, and/or how a point of interest may be scanned, by an external scan, to improve results. In a first example, comparing the shape of cancerous polyps in historical (previous) colonoscopy scans, where cancerous polyps were identified, to polyps in a current scan may help identify cancerous polyps in the current scan. Here colonoscopy may be used to describe a scan that looks for abnormalities in the colon, and may be performed by an ingestible ultrasound capsule, ingestible camera, or others. The system may also look for any anomalous readings that have been identified (such as low blood flow) in previous scans to indicate other problems that are not specifically being searched for.

In a second example, if a patient comes in with known diverticulitis, the system may compare inflammation surrounding previously identified pouches to inflammation in current scan data in order to identify pouches in a patient. Diverticulitis is the infection or inflammation of pouches that may form in your intestines. These pouches are called diverticula.

In some embodiments, method 200 may represent block 140 of method 100 (shown in FIG. 1). Method 200 may begin at 205, where current scan data from an ingestible scanning device is received. As discussed herein, current scan data may be an image (e.g., ultrasound image), medical data, signal data, etc.

At 210, a point of interest category is identified based on the current scan data or historical data. The point of interest category may be the main subject of the current scan data. Following the first example from above, for a patient coming in for a general colonoscopy with an ingestible scanning device and no symptoms, the system may look for any anomaly, identify the anomaly (such as a polyp) as a point of interest, give the point of interest one or more categories (e.g., low blood flow or asymmetric shapes), and find historical data with the one or more categories for comparison. Following the second example from above, for a patient complaining of intestinal pain and a previous diagnosis of diverticulitis, inflammation (which may surround pouches) may be the main category based on the previous diagnosis. The system may preemptively find historical data, that contains the identified categories, for comparison during the scan (e.g., comparing the characteristics of inflamed pouches).

In some embodiments, multiple categories may be identified for a single point of interest. For example, a single point of interest (e.g., a discolored area of the intestines) may be tagged with a category of low blood flow and a category of calcification.

Techniques for identifying the point of interest category may include user selection, but they may additionally include automated techniques, such as image recognition analysis (e.g., to identify objects in an image/video), anomaly recognition (e.g., to identify anomalies within an image/video), location determination (e.g., identifying a location where an image was generated, or determining a location based tissue scans/images), etc. In some embodiments, the data from the scans may have an acceptable range, any data outside the range may be identified as a point of interest. For example, a typical blood flow for the intestines may be 6-7% of the total blood flow, if the blood flow is below that range it may be identified as having a category of "low blood flow." In embodiments, neural networks may be employed to identify the point of interest category (e.g., cognitive image analysis, etc.) when current scan data falls outside of acceptable ranges. In some embodiments, the category may be based on an identified characteristic. For example, any growth protruding out of the sides of the intestines (such as a polyp) may be tagged with a category of abnormal growth. In some embodiments, a user may be notified if a point of interest is identified. For example, if a growth above a certain size is detected, an ultrasound image may be displayed with the growth highlighted.

At 215, a relevance score for the identified point of interest category is generated from the current scan data. Following the first example from above of a colonoscopy, some categories may be designated as low relevance (e.g., minor calcifications) that are not likely to cause a problem (e.g., they do not match any known problems) unless other underlying symptoms are present, whereas other categories (e.g., a large polyp) may have a high relevance (the characteristics of the point of interest match a problem closely). Following the second example from above involving diverticulitis, the system may identify inflammation as high relevance (e.g., likely to indicate a pouch) and may identify polyps as low relevance (e.g., not likely to indicate a pouch). In embodiments, a relevance score may be based on a continuum (for example, a relevance score may be somewhere between "similar" and "unrelated"), or it may be multidimensional (e.g., a point plotted within one or more 3D models where the axes define a given analyzed component of the relevance score). In some embodiments, the relevance score may be based on a threshold. For example, a normal blood flow range for the intestines may be 0.88+/−0.13 ml/min/g, where 0.75 ml/min/g would be a lower threshold. An area of the intestines with a blood flow at or just below a threshold may be tagged with a low relevance score (e.g., close to normal) for the "low blood flow" category. An area of the intestines with no blood flow may be tagged with a high relevance sore for the "low blood flow" category. In some embodiments, the relevance score may be a numerical score based on the degree of similarity between the point of interest and the category.

At 220, a set of historical scan data is identified, based on the point of interest category. In embodiments, a historical scan data repository may be pre-defined (e.g., a particular file folder on a computing device), or it may be undefined (e.g., the set of historical scan data may be fetched from the Internet, fetched by searching an entire disk drive within the computing device, by scanning multiple shared folders over multiple devices, by searching relevant historical scan data databases, etc.).

In embodiments, the set of historical scan data may have metadata tags that already describe particular data ranges that should be investigated further. In such cases, the metadata tags with appropriate actions may be identified and returned by the search. In some embodiments, the set of historical scan data may have metadata tags that indicate what further steps should be taken. For example, when a region of low blood flow is found in the intestines (for example, based on scan data received in block 205), a historical scan that found a similar blood flow may be identified. A metadata tag on the similar scan may indicate that an x-ray of the area was able to determine the cause of the historical reduced blood flow.

At block 230, the identified set of historical data may be analyzed based on features of the point of interest and the point of interest category. In some embodiments, the historical data may be analyzed to determine point of interest features (e.g., blood flow rate, tumor size, etc.) and related external information (e.g., what scan to perform, what angle should the scan be taken at, what intensity of radiation, etc.). In some embodiments, a point of interest category may be used to identify specific features in the set of historical data that may be present in the current scan data.

In some embodiments, the analyzing may include assigning a similarity score to one or more sets of data. For example, if the internal scan data received at block 205 identifies a point of interest (e.g., an anomaly), the system may take that internal scan data and compare it to the historical scan data. The closer the data in the historical scan data matches the current scan data, the higher the similarity score. In some embodiments the identified set of historical data and the current scan data may be displayed for a user. For example, if an image shows a growth that has tumor characteristics, several images of confirmed tumors may be displayed for comparison.

At block 240, a configuration for the external scan may be determined based on historical data. For instance, when an ingestible ultrasound device finds a disturbance in the tissue, such as an ulcer, a first orientation for an external scan may provide a better image than a second orientation. Historical data may show that x-rays of an ulcer from the side may provide inferior data than scans of the face of the ulcer. Likewise, historical data may be analyzed to determine the area that needs to be scanned. For example, a tumor that exhibits signs of being malignant may require a wider area external scan (for example, to determine whether a cancer has spread) than a tumor that exhibits signs of being benign.

In some embodiments, the configuration may include angle, direction, intensity, area, focus, and signal strength, among others. For example, historical data may be analyzed to determine an angle of x-ray that should be used to scan an ulcer. Some angles may provide more, or more complete, information than other angles.

At block 250, based on the first scan, a second scan (i.e., external scan) may be performed. Following the first example from above, an internal scanning device may be used to identify a polyp and information on the polyp including an orientation of the polyp. An x-ray may be performed, based on the internal scan, where the x-ray machine is oriented to give a view showing the profile of the polyp. A profile view of the polyp may give a radiologist a better chance of diagnosing whether the polyp is cancerous. Following the second example from above, an internal scanning device may be used to detect a possible diverticulitis pouch. Based on the comparison of block 230 and the configuration from block 240, an external scan (e.g., a computerized tomography (CT) scan) of the immediate area surrounding the pouch may be performed instead of a large area scan of the entire abdomen. In some embodiments, the external scan is automatically performed. In some embodiments, based on the characteristics from block 240 meeting or exceeding a threshold level, such as blood flow being below an acceptable normal range, an external scan may be performed. In some embodiments, an external scan may not be automatically performed in block 250. Rather, in some embodiments, block 250 may include prompting a user to initiate an external scan. For example, if, during a scan, the threshold is exceeded, the user may be shown the image and prompted to initiate an external scan.

In some embodiments, the threshold level may be one or more identified features. For example, certain shapes or colors may indicate that a second scan is warranted. Some shapes, e.g., polyps, may be indicative of underlying medical problems while other shapes, e.g., a small bump, may be normal. Significant discoloration may indicate an underlying condition, such as necrosis or gangrene, while a slight discoloration may be a natural variance in the flesh tone.

In some embodiments, the threshold may be a specific value exhibited by the scanned tissue. For example, the threshold value may be a blood flow rate, a density, a particular angle of curvature for a growth, or a size of a growth.

In some embodiments, the threshold may be a combination of features. For example, any area of the intestines with a blood flow below a certain rate and a temperature above a certain rate may trigger an external scan, even though that blood flow and that temperature may not individually trigger an external scan by themselves. For example, a growth of a certain shape with a blood flow above a certain rate may trigger an external scan.

Figure 3:
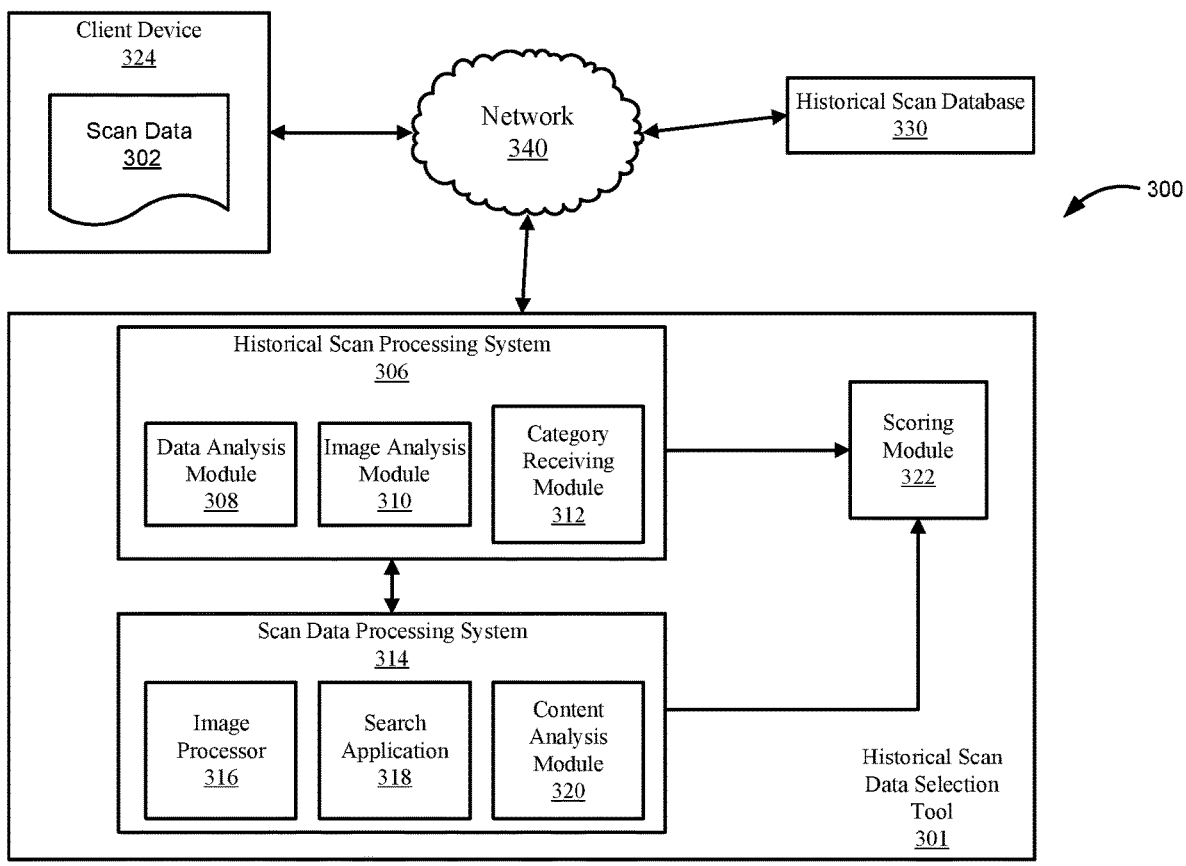
FIG. 3 is a block diagram illustrating an example networking environment according to various embodiments of the present disclosure.

Turning now to FIG. 3, illustrated is an example networking environment 300, in accordance with embodiments of the present disclosure. Networking environment 300 may include a client device 324, historical scan data database 330, network 340, and a historical scan data selection tool 301 (e.g., a system) for historical scan data selection based on point of interest category and scan type. Historical scan data selection tool 301 may be implemented as an application running on a user's computing device, as a service offered via the cloud, as a web browser plugin, as a smartphone application, or as a codependent application attached to a secondary application (e.g., as an "overlay" or a companion application to a partner application, such as a text messaging application).

Network 340 may be any type or combination of networks. For example, network 340 may include any combination of personal area network (PAN), local area network (LAN), metropolitan area network (MAN), wide area network (WAN), wireless local area network (WLAN), storage area network (SAN), enterprise private network (EPN), or virtual private network (VPN). In some embodiments, the network 340 may refer to an IP network, a conventional coaxial-based network, etc. For example, a server storing historical scan data database 330 may communicate with various client devices (e.g. tablets, laptops, smartphones, portable terminals, client device 324, etc.) over the Internet.

In some embodiments, the network 340 may be implemented within a cloud computing environment, or using one or more cloud computing services. Consistent with various embodiments, a cloud computing environment may include a network-based, distributed data processing system that provides one or more cloud computing services. Further, a cloud computing environment may include many computers (e.g., hundreds or thousands of computers or more) disposed within one or more data centers and configured to share resources over the network 340. Cloud computing is discussed in greater detail in regard to FIGS. 5 & 6.

Client device 324 may be a desktop, laptop, smartphone, tablet, or any other suitable computing device for a user to interact with and execute the methods/techniques described herein. In embodiments, client device 324 may store one or more sets of scan data, such as scan data 302. As described herein, scan data 302 may be a written article, an audio stream, a video stream, etc.

Historical scan data database 330 may store a wide variety of historical scan data, as contemplated herein. For example, historical scan data may include scan data, still images, videos, audio recordings (e.g., heart beat from a sonogram), or any other type of historical scan data an author/user of scan data 302 may wish to add or use in conjunction with scan data 302. In embodiments, historical scan data database 330 may reside on a single server, on multiple servers within a cloud computing environment, and/or on the client device 324 or on the same physical system or virtualized system as historical scan data selection tool 301.

Historical scan data selection tool 301 may be a standalone computing system, such as a desktop or laptop; a server; or a virtualized system running on one or more servers within a cloud computing environment. Historical scan data selection tool 301 may include historical scan data processing system 306, scan data processing system 314, and scoring module 322.

In embodiments, scan data 302 may be received at by the historical scan data selection tool 301 via the network 340. The scan data processing system 314 may include, e.g., an image processor 316, a search application 318, and a content analysis module 320.

In embodiments, the image processor 316 may be configured to analyze historical scans to identify one or more point of interest categories. In embodiments, image processor 316 may further be configured to receive identify features of anomalies, from which point of interest categories may then be identified.

As point of interest categories are identified, relevance scores may be generated to determine one or more features (signal strength, density, shape of an abnormality, size of an abnormality, blood flow, etc.), of the historical scan data with regard to the identified point of interest category via content analysis module 320. In embodiments, content analysis module 320 may include, or store information in, a relational database linking one or more features to one or more other features. For example, points of interest may have a higher temperature combined with increased blood flow, where either individually may not be an abnormality. In other embodiments, content analysis module 320 may include a convolutional neural network to generate a relevance score. In yet other embodiments, the content analysis module 320 may include, for example, both a relational database and a convolutional neural network, and may use the data from the relational database as input for the convolutional neural network. Relevance scores may be output to scoring module 322 for similarity scoring.

Search application 318 may be employed to find a set of historical scan data by searching historical scan data database 330 for the point of interest category identified by image processor 316. As described herein, historical scan data database 330 may include a pre-defined file folder or computer, or it may be construed as a collection of websites, computers, servers, etc. Search results may be returned to the historical scan data processing system 306.

In some embodiments, the historical scan data processing system 306 may include, e.g., a data analysis module 308, an image analysis module 310, and a category receiving module 312. The category receiving module 312 may be configured to receive, from the scan data processing system 314, point of interest categories identified by analyzing areas of scan data 302 that are necessarily related to the set of historical scan data retrieved by search application 318.

For example, in embodiments, shape recognition may be employed, as part of scan data processing system 314, to identify a particular growth or formation. A superclass for the growth or formation may be determined by parsing a relational database for the shape, and the superclass may be assigned as a point of interest category. After identifying point of interest categories, the scan data processing system 314 may transmit data regarding the point of interest categories to the category receiving module 312, as the shape attributes may inform the identification of visual/audio attributes by the image analysis module 310, or data analysis module 308, respectively.

Based on digital file formats (e.g., image file formats (e.g., .jpg), textual formats (e.g., .docx, .raf, .txt, etc.), audio formats (e.g., .mp3, etc.), and video file formats (e.g., .wmv)), historical scan data processing system 306 may determine with which processing module (e.g., data analysis module 308 or image analysis module 310) the system should use to analyze the historical scan data received in response to the search application 318's results. In embodiments where textual historical scan data is received, analysis of the historical scan data may be performed at, for example, scan data processor 316. In other embodiments, historical scan data processing system 306 may include its own scan data processor (not shown).

In embodiments, image analysis module 310 may be configured to receive video and image formats to identify objects, locations, points of interest, etc. (e.g., subjects) within images, as described herein. In embodiments where a video file is received, still frame images may be selected at random intervals, at regular intervals, or a "best image" (e.g., image that shows a tumor most clearly) may be selected according to still image selection criteria.

In embodiments, image analysis module 310 may be configured to identify (e.g., from a still image, a video, or a single frame of a video feed), an object or feature (e.g., shape of a growth, coloration, inflammation, etc.). Image analysis module 310 may further identify, given the combination of objects in the image, the context of the image. For example, an image with a combination of objects including one or more shapes, growths, discolorations may provide the basis for identifying the context of the image as a necrosis. Image analysis module 310 may perform the analysis techniques described herein to output a probability of a particular point of interest for an analyzed image, based on the received point of interest category.

Once the objects, attributes, context, and relevance score of an image have been identified, the image may be "tagged" or otherwise annotated with a list or table reflecting this information (e.g., as metadata) and stored in historical scan data database 330. Relevance scores generated by image analysis module 310 are sent to scoring module 322.

In embodiments, as discussed herein, scoring module 322 may be used to generate similarity scores based on the received relevance scores for both the content and the historical scan data, as discussed herein.

In embodiments, scoring module 322 may employ a neural network to generate similarity scores, as described herein. In embodiments, a neural network may be a multi-layer perceptron, a system of sigmoid neurons, a directed acyclic graph comprising a plurality of corelets, or any other structure/system capable of neural networking.

Scoring module 322 may select, based on the similarity scores, one or more images from the historical scan data to display to the user, as described herein. The parameters for the selection may include a single dataset with the greatest similarity score, or it may be a subset of historical scan data (e.g., the ten historical scan data with the greatest similarity scores). Selection parameters may be adjustable.

Figure 4:
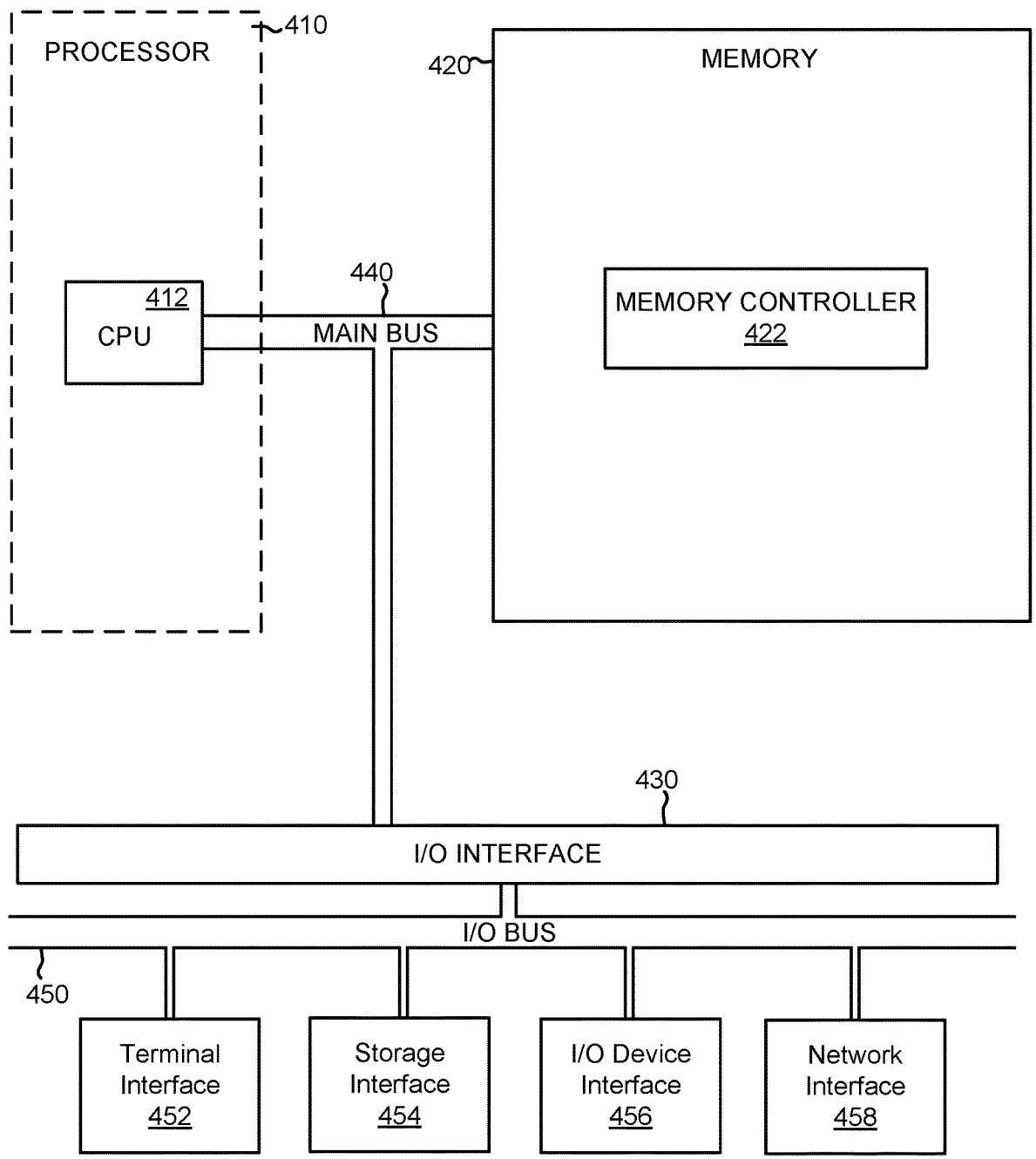
FIG. 4 depicts a computer system according to various embodiments of the present disclosure.

FIG. 4 depicts the representative major components of an exemplary Computer System 401 that may be used in accordance with embodiments of the present disclosure. The particular components depicted are presented for the purpose of example only and are not necessarily the only such variations. The Computer System 401 may comprise a Processor 410, Memory 420, an Input/Output Interface (also referred to herein as I/O or I/O Interface) 430, and a Main Bus 440. The Main Bus 440 may provide communication pathways for the other components of the Computer System 401. In some embodiments, the Main Bus 440 may connect to other components such as a specialized digital signal processor (not depicted).

The Processor 410 of the Computer System 401 may be comprised of one or more CPUs 412. The Processor 410 may additionally be comprised of one or more memory buffers or caches (not depicted) that provide temporary storage of instructions and data for the CPU 412. The CPU 412 may perform instructions on input provided from the caches or from the Memory 420 and output the result to caches or the Memory 420. The CPU 412 may be comprised of one or more circuits configured to perform one or methods consistent with embodiments of the present disclosure. In some embodiments, the Computer System 401 may contain multiple Processors 410 typical of a relatively large system. In other embodiments, however, the Computer System 401 may be a single processor with a singular CPU 412.

The Memory 420 of the Computer System 401 may be comprised of a Memory Controller 422 and one or more memory modules for temporarily or permanently storing data (not depicted). In some embodiments, the Memory 420 may comprise a random-access semiconductor memory, storage device, or storage medium (either volatile or non-volatile) for storing data and programs. The Memory Controller 422 may communicate with the Processor 410, facilitating storage and retrieval of information in the memory modules. The Memory Controller 422 may communicate with the I/O Interface 430, facilitating storage and retrieval of input or output in the memory modules. In some embodiments, the memory modules may be dual in-line memory modules.

The I/O Interface 430 may comprise an I/O Bus 450, a Terminal Interface 452, a Storage Interface 454, an I/O Device Interface 456, and a Network Interface 458. The I/O Interface 430 may connect the Main Bus 440 to the I/O Bus 450. The I/O Interface 430 may direct instructions and data from the Processor 410 and Memory 420 to the various interfaces of the I/O Bus 450. The I/O Interface 430 may also direct instructions and data from the various interfaces of the I/O Bus 450 to the Processor 410 and Memory 420. The various interfaces may comprise the Terminal Interface 452, the Storage Interface 454, the I/O Device Interface 456, and the Network Interface 458. In some embodiments, the various interfaces may comprise a subset of the aforementioned interfaces (e.g., an embedded computer system in an industrial application may not include the Terminal Interface 452 and the Storage Interface 454).

Logic modules throughout the Computer System 401—including but not limited to the Memory 420, the Processor 410, and the I/O Interface 430—may communicate failures and changes to one or more components to a hypervisor or operating system (not depicted). The hypervisor or the operating system may allocate the various resources available in the Computer System 401 and track the location of data in Memory 420 and of processes assigned to various CPUs 412. In embodiments that combine or rearrange elements, aspects of the logic modules' capabilities may be combined or redistributed. These variations may be apparent to one skilled in the art.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium may be a tangible device that may retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that may direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
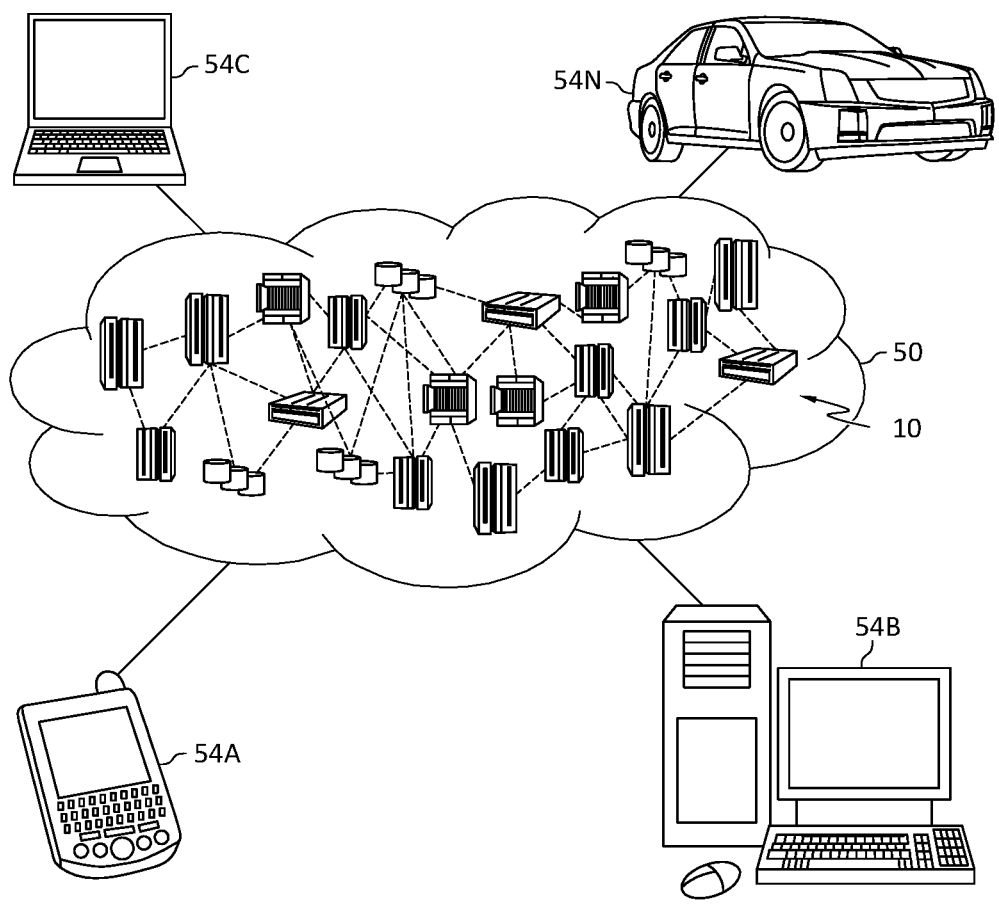
FIG. 5 depicts a cloud computing environment according to an embodiment of the present disclosure.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
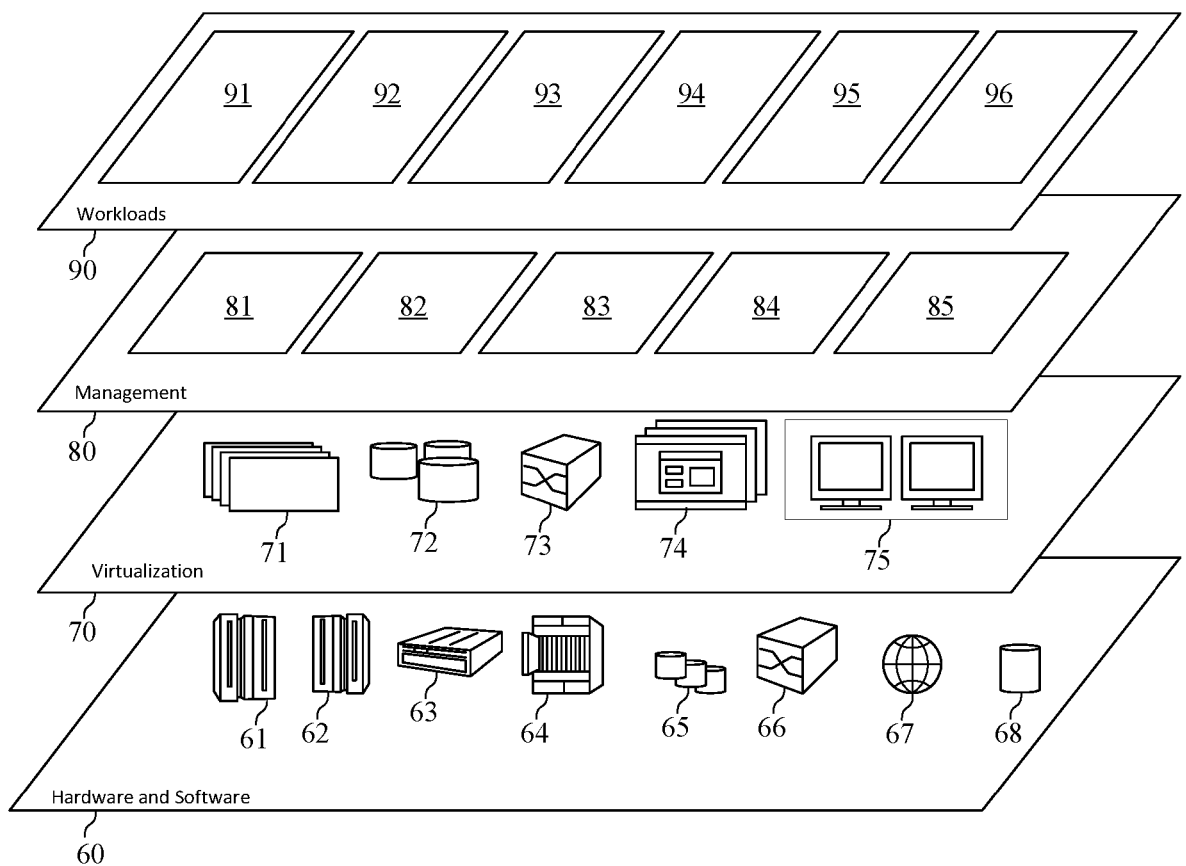
FIG. 6 depicts abstraction model layers according to an embodiment of the present disclosure.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and predictive neural networks 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, a "set" of an object does not equate to all available instances of that object. For example, if four files were available, a set of files may not contain all four files. Further, as used herein, the phrase "each of a set" of an object refers only to the instances of that object of that set. For example, if four files were available, the phrase "a set of two files from the four files, each of the files in the set being read only" would properly be interpreted as implying that two files (the two files in the set) are read only. The two files of the four available files that are not in the set may or may not be read only.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method comprising:
    receiving a first set of data from an ingestible scanner inside a body of a patient at a first moment in time;
    identifying a point of interest within the body based on the first set of data;
    determining a location of the point of interest within the body in relation to the ingestible scanner;
    directing an external scanner to the point of interest identified with the first set of data from the ingestible scanner based on the location of the point of interest in relation to the ingestible scanner; and
    scanning the point of interest with the external scanner at the first moment in time.

2. The method of claim 1, wherein the determining is performed by a technique selected from the group consisting of echolocation, doppler location, x-ray scan, and triangulation.

3. The method of claim 1, wherein the ingestible scanner is an ingestible ultrasonic scanner and the external scanner is an x-ray scanner.

4. The method of claim 1, further comprising:
determining a configuration of the external scanner based on the first set of data.

5. The method of claim 4, wherein the configuration includes an angle of the external scanner relative to the point of interest.

6. The method of claim 4, wherein the configuration includes an area of exposure for the external scanner.

7. The method of claim 4 wherein the determining further includes:
determining a category for the point of interest;
receiving a set of historical data based on the category;
comparing the first set of data to the historical data; and
configuring the external scan based on the comparing.

8. The method of claim 7, wherein the set of historical data includes a type of external scan and a configuration of the external scan.

9. The method of claim 1, wherein the point of interest is automatically scanned with the external scanner at the first moment in time.

10. A computer program product, the computer program product comprising a computer readable storage medium having program instructions embodied therewith, the program instructions executable by a computer to cause the computer to:
receive a first set of data from an ingestible scanner inside a body of a patient at the first moment in time;
identify a point of interest within the body based on the first set of data;
determine a location of the point of interest within the body in relation to the ingestible scanner;
directing an external scanner to the point of interest identified with the first set of data from the ingestible scanner based on the location of the point of interest in relation to the ingestible scanner; and
scan the point of interest with the external scanner at the first moment in time.

11. The computer program product of claim 10, wherein the determining is performed by a technique selected from the group consisting of echolocation, doppler location, x-ray scan, and triangulation.

12. The computer program product of claim 10, wherein the ingestible scanner is an ingestible ultrasonic scanning device and the external scanner is an x-ray scanner.

13. The computer program product of claim 10, further comprising:
determining a configuration of the external scanner based on the first set of data.

14. The computer program product of claim 13, wherein the configuration includes an angle of the external scanner relative to the point of interest.

15. The computer program product of claim 13, wherein the configuration includes an area of exposure for the external scanner.

16. The computer program product of claim 13, wherein the determining further includes:
determining a category for the point of interest;
receiving a set of historical data based on the category;
comparing the first set of data to the historical data; and
configuring the external scan based on the comparing.

17. A system comprising:
a processor; and
a memory in communication with the processor, the memory containing program instructions that, when executed by the processor, are configured to cause the processor to perform a method, the method comprising:
receiving a first set of data from an ingestible scanner inside a body of a patient;
identifying a point of interest within the body based on the first set of data at a first moment in time;
determining a location of the point of interest within the body in relation to the ingestible scanner;
directing an external scanner to the point of interest identified with the first set of data from the ingestible scanner based on the location of the point of interest in relation to the ingestible scanner; and
scanning the point of interest with the external scanner at the first moment in time.

18. The system of claim 17, wherein the determining is performed by a technique selected from the group consisting of echolocation, doppler location, x-ray scan, and triangulation.

19. The system of claim 17, wherein the ingestible scanner is an ingestible ultrasonic scanning device and the external scanner is an x-ray scanner.

20. The system of claim 17, further comprising:
determining a configuration of the external scanner based on the first set of data.

* * * * *